United States Patent [19]

Biola et al.

[11] 4,219,389

[45] Aug. 26, 1980

[54] SEPARATION OF ACRYLIC ACID FROM SOLUTIONS THEREOF IN TRI-N-BUTYL PHOSPHATE

[75] Inventors: Georges Biola, Bron; Yves Komorn, Lyons; Gerard Schneider, Caluire, all of France

[73] Assignee: Rhone-Poulenc Industries, Paris, France

[21] Appl. No.: 914,923

[22] Filed: Jun. 12, 1978

[30] Foreign Application Priority Data

Jun. 14, 1977 [FR] France ................................ 77 18136

[51] Int. Cl.$^2$ ......................... C07C 51/44; B01D 1/22
[52] U.S. Cl. ........................................ 203/72; 203/75; 203/77; 562/600
[58] Field of Search ........................ 562/600, 598, 599; 203/72, 75, 89, DIG. 21, 77, 81, 82

[56] References Cited

U.S. PATENT DOCUMENTS

| | | | |
|---|---|---|---|
| 3,092,587 | 6/1963 | Ester et al. ............................. | 203/72 |
| 3,432,401 | 3/1969 | Tcherkawsky ...................... | 562/600 |
| 3,644,179 | 2/1972 | Knoer et al. ........................... | 203/72 |
| 3,697,387 | 10/1972 | Munch .................................. | 203/72 |
| 3,859,175 | 1/1975 | Ohrui et al. .......................... | 562/600 |
| 4,043,873 | 8/1977 | Ackermann et al. .................. | 203/72 |

FOREIGN PATENT DOCUMENTS 1558432 1/1969 France .

Primary Examiner—Wilbur L. Bascomb, Jr.
Attorney, Agent, or Firm—Burns, Doane, Swecker & Mathis

[57] ABSTRACT

Acrylic acid is separated from its solutions in tri-n-butyl phosphate by establishing from such a solution a vapor phase comprising substantially all of the acrylic acid and a portion of the solvent, at a temperature below the degradation point of the acrylic acid; next partially or totally condensing said vapor phase; and then distilling the acrylic acid from such condensation product, while maintaining an amount of acrylic acid at the base of the distillation column, and conducting the distillation under conditions such that neither solvent degradation nor acrylic acid crystallization results.

10 Claims, 1 Drawing Figure

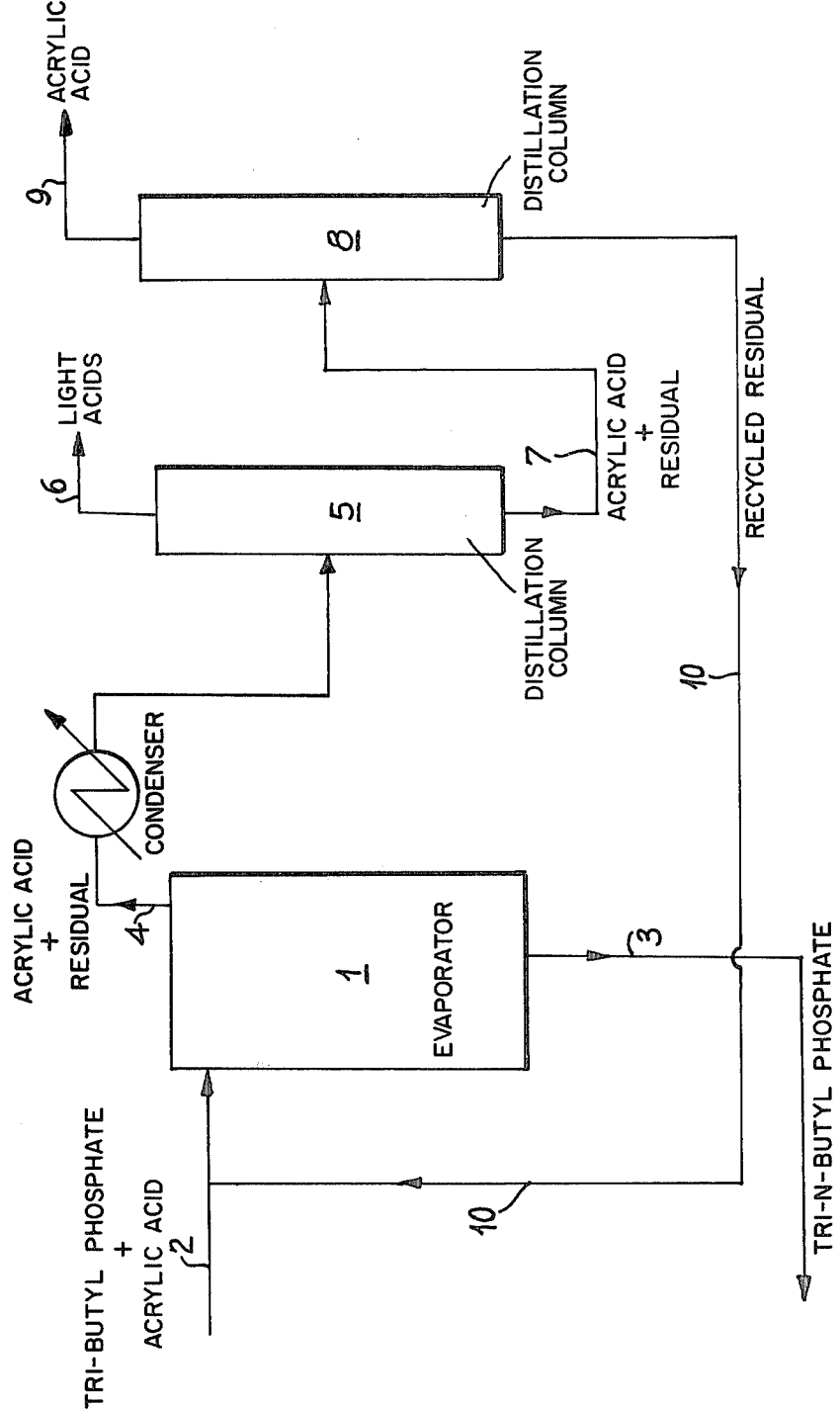

SEPARATION OF ACRYLIC ACID FROM SOLUTIONS THEREOF IN TRI-N-BUTYL PHOSPHATE

BACKGROUND OF THE INVENTION

1. Field of the Invention

The present invention relates to a process for the separation of acrylic acid from its solutions in tri-n-butyl phosphate, and, more especially, relates to such process which is carried out utilizing a unique distillation technique.

2. Description of the Prior Art

It is well known to this art that the separation of acrylic acid from its production reaction media, for example, from the raw reaction product of the oxidation of propylene and/or acrolein, is a delicate and vexing problem and numerous processes have to date been proposed to effect such separation. Specifically, a technique for the absorption in gaseous phase or extraction in liquid phase of the acrylic acid by means of different solvents is known. The acrylic acid is then isolated by distillation, or directly esterified in the extraction medium. Compare French Pat. No. 1,558,432 [Dec. 14, 1967] and French Pat. No. 1,452,566 [Nov. 5, 1965].

Among those solvents already employed for the above purpose, tri-n-butyl phosphate is particularly efficient. But separation of the acid from its solutions in this solvent encounters numerous difficulties. In fact, tributyl phosphate is subject to degradation when exposed to elevated temperatures, especially in the presence of acids or of water, so that depletion in acrylic acid of the solutions at a normal or slightly reduced pressure by distillation results in a significant loss of solvent. On the other hand, in order to obtain a good yield of acrylic acid absorbed or extracted with the aid of tributyl phosphate recycled after distillation, it is necessary that the phosphate have an acrylic acid content as low as possible. To avoid the degradation of the solvent and to lower its acrylic acid content as much as possible, it may be envisaged to perform the distillation in a stronger vacuum. However, in this case difficulties are encountered in the recovery of the acrylic acid, because of its relatively high crystallization point (13.5° C.), corresponding to a vapor pressure of but a few mm. of mercury.

SUMMARY OF THE INVENTION

There has now been found according to this invention a process which remedies the difficulties mentioned above to the extent that it permits [1] the ready separation of acrylic acid, [2] the recovery of tri-n-butyl phosphate substantially devoid of acid and [3] the avoidance of degradation of the phosphate. Other advantages of the process will appear in the description which follows.

Briefly, a primary object of this invention is to provide for the separation of acrylic acid from its solutions in tri-n-butyl phosphate, said separation comprising (i) establishing vapor phase containing substantially all of the acid and a portion of the tri-n-butyl phosphate, by heating the initial liquid under conditions which preclude the degradation of tri-n-butyl phosphate; (ii) distillation of the acrylic acid, following the partial or total condensation of the vapor phase, while maintaining in the bottom of the distillation column an acrylic acid content such that operating conditions which avoid the degradation of the tri-n-butyl phosphate and the crystallization of the acrylic acid at the head of the column, are maintained; and (iii) ultimately, and preferably, recycling the residue of the distillation to the first stage.

BRIEF DESCRIPTION OF THE DRAWING

The FIGURE of drawing is a schematic representation of apparatus suitable for conducting the process of the invention.

DETAILED DESCRIPTION OF THE INVENTION

The initial solution may be of any origin whatsoever. It may result, for example, from the absorption of acrylic acid by tri-n-butyl phosphate from a gaseous mixture obtained from the oxidation of propylene and/or acrolein, such as described in French Pat. No. 1,558,432 mentioned above. It may also originate from the liquid-liquid extraction of aqueous solutions of acrylic acid by tri-n-butyl phosphate. It may contain, without causing difficulties, minor amounts of other organic acids lighter than the acrylic acid, in particular acetic acid, formed simultaneously with the acrylic acid and entrained by the solvent. As will later be seen, these acids are readily separated in a complementary stage within the framework of the process of the invention. Also, if during the operations of absorption or extraction of the acrylic acid by tributyl phosphate, acrolein and/or water have been entrained, it is advantageous to free the solution of these compounds prior to performing the process of the invention, for example, by heating, optionally gas injection.

The concentration of the acrylic acid in the beginning solution is immaterial, because the process of the invention is applicable with the same efficiency to both concentrated and dilute acrylic acid solutions. Purely for purposes of example, it may be said that the initial solution may contain 5 to 50% by weight of acrylic acid.

In the first operational stage of the method of the invention, a vapor phase comprising substantially all of the acrylic acid and a portion of the tri-n-butyl phosphate is established by heating the initial liquid under conditions which avoid the degradation of the tri-n-butyl phosphate. In this respect, the maximum temperature employed represents an essential factor. A temperature of 160° C. should not be exceeded, and most preferably the temperature ranges between about 110° and 150° C. The duration of the heating period is also of some importance and must be controlled; the reaction time is inversely proportional to the temperature applied. For the temperature range given above, retention times of between approximately 30 minutes and 5 seconds are generally adequate to establish a vapor phase containing, according to the invention, virtually all of the acrylic acid and a fraction of the tributyl phosphate without degradation of the solvent either in the liquid or vapor phase.

The pressure to be applied is a function of the other operating conditions; its determination is thus within the capability of those skilled in the art. As an indication, it may be said that one should contact the process preferably at a pressure lower than atmospheric, within the range typically between about 1 and 30 mm. of mercury.

In practice, in one embodiment of the first operational stage, which may comprise one or a plurality of phases, various means of known type and permitting vaporization under the conditions described above may be used: for example, a series of continuous and instantaneous vaporizations may be performed, or a column of a series of heating plates may be used for vaporization, or, preferably, use may be made of the well-known thin film evaporation technique [see, for example, M. Loncin, "Unit Operations of Chemical Engineering", pp. 408–411] or, these several techniques may be used in combination.

The liquid remaining after this stage of vaporization essentially consists of tri-n-butyl phosphate subtantially free of acrylic acid and any other light organic acid that may have been present in the original solution. Obtaining tri-n-butyl phosphate free of organic acids represents one of the especial advantages of the process of the invention. In fact, due to the rapid recovery of a significant fraction of the solvent, same is exposed to the deleterious effects of heat for a minimum period of time and the optimum conditions to avoid the degradation of the phosphate are attained. In addition, because the solvent recovered does not contain the acid, it may be recycled directly into the operations of extraction or absorption of the acrylic acid from solutions or from a gas in which same is contained, thus producing maximum yields from the extraction or absorption.

According to the second operational stage of the process of the invention, the vapor phase formed in the first stage is subjected, after partial or total condensation, to a distillation yielding high purity acrylic acid. The temperature conditions prevailing in the distillation step are critical. Indeed, the boiling point of the liquid must not exceed the temperature at which the tri-n-butyl phosphate is appreciably degraded, i.e., approximately 160° C. The most advantageous temperature range is between 120° and 150° C. This result cannot be attained in the classical manner by a sufficient reduction in pressure, because the acrylic acid crystallizes in the condenser head when the pressure prevailing in the column is reduced to a value less than 5 mm Hg. According to a fundamental feature of the invention, an amount of acrylic acid sufficient to perform the distillation under the temperature conditions desired, is maintained at the base of the distillation column. The quantity of acrylic acid to be maintained in the solution may be between 1 and 20%, preferably 2 to 10% for the temperature range above noted. As in the preceding stage, the retention time has a certain importance. It is again an inverse function of the temperature. For a temperature of 120° to 150° C., it is comprised between 1 hour and 30 seconds. The pressure is adjusted as a function of the temperature and of the acrylic acid content selected in each particular case and its determination is within the skill in the art. A range comprised between 5 and 30 mm. Hg. is generally applicable in all cases. The liquid issuing from the base of the column, composed of tri-n-butyl phosphate and a certain amount of acrylic acid, is advantageously recycled to the vaporization stage, which constitutes the first stage of the process of the invention. The advantage of this recycling is readily understood; it makes it possible to recover, in the overall process, all of the acrylic acid and tri-n-butyl phosphate contained in the initial solution. One embodiment of the process comprises the control of the operation of the distillation column so that the liquid issuing at the base of the column and recycled to the first stage has a concentration of the same order as the initial solution. However, this particular embodiment is not critical and it is suitable to process initial and recycled solutions having different compositions.

It will be appreciated that it is within the scope of the invention not to recycle the liquid withdrawn from the base of the distillation column to the first stage in the operation, but rather to use such liquid from another application.

The process of the invention too may comprise yet other embodiments, whether separately or in combination. According to one such embodiment if the initial solution contains, in addition to the acrylic acid, other light organic acids, particularly acetic acid, said acid is distilled in a supplementary stage. This separation is performed prior to the distillation of the acrylic acid. Temperature and pressure conditions are similar to those employed for the distillation of the acrylic acid, i.e., it is necessary to utilize a temperature at the base of the column which will not induce the degradation of the tributyl phosphate and not to reduce the pressure to a point where crystallization of the acetic acid occurs. A temperature on the order of 120°–150° C. and a pressure of 30 to 100 mm. of mercury are favorable working conditions.

According to yet another embodiment, which is particularly advantageous when the process is applied to relatively highly concentrated acetic acid solutions, all or a portion of the solution to be treated is introduced downstream from the vaporizing device, preferably in the distillation column itself, at a level where the acrylic acid concentration is substantially identical to that of the feed solution. Part of the acrylic acid distills off and the liquid remaining at the base of the column is passed to the vaporizing device. In sum, the overall operating cycle otherwise is unchanged.

It is also possible to introduce in the fluid circuit, for example, in the lead condenser of the distillation column or columns, polymerization inhibitors of known type, such as hydroquinone, the methyl ether of hydroquinone, and the like.

The invention will be better understood with reference to the following description of one embodiment of the process, in which reference is made to the FIGURE of drawing. Into the vaporizing device 1, for example, a thin film evaporator, is fed a solution to be treated, by means of the conduit 2. At the base of the device 1, the tri-n-butyl phosphate, freed of acrylic acid or any other acid potentially present, is withdrawn and charged through the line 3 to the acrylic acid absorption or extraction stage, upstream of the process of the invention. The vapor phase containing the acrylic acid and possibly light acids such as acetic acid, also a certain amount of tri-n-butyl phosphate, exits from the device 1 by the conduit 4 and is introduced, after total or partial condensation, into the column 5 where the acetic acid is conveyed to the head and is recovered via the piping 6. The remaining liquid phase flows through the conduit 7 and feeds the distillation column 8 where the acrylic acid exits through 9, while the liquid withdrawn at the base of the column is recycled through the conduit 10 to feed the device 1. The column 5 is optional and is eliminated if the feed solution does not contain acids other than the acrylic acid. The process of the present invention may be continuous or discontinuous.

In order to further illustrate the present invention and the advantages thereof, the following specific example is given, it being understood that same is intended only as illustrative and in nowise limitative.

EXAMPLE

In this example, reference is made to the diagram of the figure of drawing. The thin film evaporator 1 was fed through the pipe 2 with 108.78 parts by weight of a mixture containing 6.52% by weight of acrylic acid, 93.30% tributyl phosphate, 0.01% water and 0.17% acetic acid. In the mixture, 82.66 parts originated from a system for the absorption of acrylic acid by tri-n-butyl phosphate and 26.12 parts, by recycling through the conduit 10. The evaporator 1 was maintained, by means of suitable regulators, under a pressure of 5 mm. of mercury and at a temperature of 128° C. Separation into a liquid fraction and a vapor fraction was effected. The liquid fraction withdrawn through 3 at the base of the device, represents 76.77 parts containing 0.1% by weight of acrylic acid and 99.9% of tributyl phosphate. The liquid, after suitable cooling, was returned to the apparatus for the extraction of the acrylic acid.

The vapor fraction issuing from 4, following partial or total condensation, was conveyed to the distillation column 5. It represented 32.01 parts by weight containing 21.90% by weight of acrylic acid, 77.46% tributyl phosphate, 0.59% acetic acid and 0.03% water. The column 5 was operated under a pressure of 35 mm. mercury at its head and 42 mm. at its base, corresponding to the respective temperatures of 40° and 120° C. The presence of the tributyl phosphate permitted the separation at the apparatus head through 6 of 0.19 parts by weight of an effluent containing 89.47% by weight of acetic acid, with 5.26% acrylic acid and 5.26% water. The liquid exiting from the base of the column via line 7 represented 31.82 parts by weight containing 77.94% tributyl phosphate, 22.00% acrylic acid and 0.06% acetic acid.

The product was conveyed to the column 8 operating under a pressure of 10 mm. of mercury at its head and 12 mm. at its base. The respective temperatures were 40° and 130° C.

The fraction at the head 9 of the apparatus of 5.7 parts by weight corresponded to a production of acrylic acid of 99.65% purity. The effluent which flowed through 10 and comprising 95.95% tributyl phosphate and 5.05% acrylic acid, was recycled to the inlet of the installation 1.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the separation and recovery of essentially pure acrylic acid and essentially pure tri-N-butyl phosphate from a solvent solution thereof, which comprises (i) vaporizing a feed stream of acrylic acid/tri-N-butyl phosphate solvent solution at a temperature not in excess of 160° C., such as to avoid degradation of the tri-N-butyl phosphate, and, whereby there is thus established (ii) a vapor phase comprising virtually all of the acrylic acid and a fraction of the tri-N-butyl phosphate solvent and (iii) a liquid phase consisting essentially of said tri-N-butyl phosphate solvent; (iv) recovering said liquid phase (iii); (v) at least partially condensing said vapor phase (ii); and thence (vi) distilling the condensate (v) at a temperature not in excess of 160° C. and under such reduced pressure as to avoid acrylic acid crystallization, to obtain a distillate (vii) comprising essentially pure acrylic acid and an acrylic acid/tri-N-butyl phosphate distilland (viii), while maintaining the amount of acrylic acid in said distilland (viii) to between 1 and 20%.

2. The process as defined by claim 1, further comprising recycling said distilland (viii) to the acrylic acid/tri-N-butyl phosphate feed stream.

3. The process as defined by claims 1 or 2, wherein the temperature of vaporization ranges between about 110° and 150° C.

4. The process as defined by claim 3, wherein the temperature of vaporization is maintained from between about 5 seconds and 30 minutes, under a pressure of from about 1 to 30 mm. Hg.

5. The process as defined by claim 1, said vaporization (i) being via thin film evaporation.

6. The process as defined by claim 4, wherein the distillation (vi) is at a temperature of from about 120° to 150° C., under a pressure of from about 5 to 30 mm. Hg., for from about 30 seconds to one hour.

7. The process as defined by claim 6, wherein the feed stream contains from about 5 to 50% by weight acrylic acid.

8. The process as defined by claim 7, the amount of acrylic acid maintained in the distilland (viii) being between 2 and 10%.

9. The process as defined by claim 6, wherein the feed stream comprises a light organic acid in addition to the acrylic acid.

10. The process as defined by claim 9, said light organic acid being acetic acid.

* * * * *